United States Patent
O'Brien et al.

(10) Patent No.: US 7,070,576 B2
(45) Date of Patent: Jul. 4, 2006

(54) DIRECTIONAL CUTTING BALLOON

(75) Inventors: Dennis O'Brien, Oceanside, CA (US); James Hantske, Murrieta, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 52 days.

(21) Appl. No.: 10/836,008

(22) Filed: Apr. 30, 2004

(65) Prior Publication Data

US 2005/0245864 A1    Nov. 3, 2005

(51) Int. Cl.
*A61M 29/00* (2006.01)

(52) U.S. Cl. .................................. 604/96.01

(58) Field of Classification Search ............. 604/96.01, 604/98; 606/159, 167, 170, 191, 192, 194
See application file for complete search history.

(56) References Cited

U.S. PATENT DOCUMENTS

| | | | |
|---|---|---|---|
| 3,811,448 A * | 5/1974 | Morton | 604/102.02 |
| 4,307,722 A | 12/1981 | Evans | |
| 4,784,636 A | 11/1988 | Rydell | |
| 4,909,252 A * | 3/1990 | Goldberger | 606/194 |
| 4,921,483 A | 5/1990 | Wijay et al. | |
| 4,966,604 A | 10/1990 | Reiss | |
| 5,053,044 A | 10/1991 | Mueller et al. | |
| 5,112,305 A | 5/1992 | Barath et al. | |
| 5,112,900 A | 5/1992 | Buddenhagen et al. | |
| 5,141,494 A | 8/1992 | Danforth et al. | |
| 5,156,610 A | 10/1992 | Reger | |
| 5,181,920 A | 1/1993 | Mueller et al. | |
| 5,196,024 A | 3/1993 | Barath | |
| 5,226,887 A | 7/1993 | Farr et al. | |
| 5,250,059 A | 10/1993 | Andreas et al. | |
| 5,273,536 A | 12/1993 | Savas | |
| 5,320,634 A | 6/1994 | Vigil et al. | |
| 5,338,300 A * | 8/1994 | Cox | 604/103.05 |
| 5,348,538 A | 9/1994 | Wang et al. | |
| 5,395,311 A | 3/1995 | Andrews | |
| 5,403,340 A | 4/1995 | Wang et al. | |
| 5,447,497 A | 9/1995 | Sogard et al. | |
| 5,453,076 A * | 9/1995 | Kiyota et al. | 600/18 |
| 5,487,319 A | 1/1996 | Cody | |
| 5,527,325 A | 6/1996 | Conley et al. | |
| 5,549,552 A | 8/1996 | Peters et al. | |
| 5,550,180 A | 8/1996 | Elsik et al. | |
| 5,556,383 A | 9/1996 | Wang et al. | |
| 5,575,771 A * | 11/1996 | Walinsky | 604/96.01 |
| 5,616,149 A | 4/1997 | Barath | |
| 5,681,281 A * | 10/1997 | Vigil et al. | 604/103.01 |
| 5,697,944 A | 12/1997 | Lary | |

(Continued)

*Primary Examiner*—Manuel Mendez
(74) *Attorney, Agent, or Firm*—Vidas, Arrett & Steinkraus, P.A.

(57) ABSTRACT

A directional cutting balloon for incising an eccentric lesion in a body conduit includes an inflatable balloon having a distal end and a proximal end. The distal balloon end is attached to a distal tube and the proximal balloon end is attached to a proximal tube. The distal tube is formed with a guidewire lumen and substantially centered along a guidewire axis. The balloon, which is typically formed with a cylindrical working section that defines a balloon axis, is offset from the guidewire axis. Specifically, when the balloon is inflated, the balloon axis is aligned parallel to and offset from the guidewire axis. One or more elongated incising elements are mounted longitudinally on the balloon. During a balloon inflation, the balloon expands eccentrically relative to the guidewire axis to thereby advance the incising element in a pre-selected direction and into an eccentric lesion.

14 Claims, 3 Drawing Sheets

U.S. PATENT DOCUMENTS

| | | |
|---|---|---|
| 5,718,684 A | 2/1998 | Gupta |
| 5,792,158 A | 8/1998 | Lary |
| 5,797,935 A | 8/1998 | Barath |
| 5,830,182 A | 11/1998 | Wang et al. |
| 5,951,941 A | 9/1999 | Wang et al. |
| 6,007,517 A * | 12/1999 | Anderson .............. 604/103.04 |
| 6,048,332 A * | 4/2000 | Duffy et al. ........... 604/103.08 |
| 6,102,904 A | 8/2000 | Vigil et al. |
| 6,146,356 A | 11/2000 | Wang et al. |
| 6,171,278 B1 | 1/2001 | Wang et al. |
| 6,197,013 B1 * | 3/2001 | Reed et al. ................. 604/509 |
| 6,258,108 B1 | 7/2001 | Lary |
| 6,328,925 B1 | 12/2001 | Wang et al. |
| 6,406,457 B1 | 6/2002 | Wang et al. |
| 6,428,552 B1 | 8/2002 | Sparks |
| 6,468,227 B1 * | 10/2002 | Zimmon ..................... 600/564 |
| 6,517,514 B1 | 2/2003 | Campbell |
| 6,632,231 B1 | 10/2003 | Radisch, Jr. |
| 6,652,568 B1 * | 11/2003 | Becker et al. .............. 623/1.11 |
| 6,682,556 B1 * | 1/2004 | Ischinger ................... 623/1.35 |

* cited by examiner

DIRECTIONAL CUTTING BALLOON

FIELD OF THE INVENTION

The present invention pertains generally to medical catheters and medical catheter procedures. More particularly, the present invention pertains to medical catheters for incising biological materials in a body conduit. The present invention is particularly, but not exclusively, useful as a cutting balloon for incising lesions in the human vasculature.

BACKGROUND OF THE INVENTION

Coronary artery stenosis is primarily due to deposits of cholesterol, calcium and fibrotic tissue, with the fibrotic tissue typically being the dominant of the three components. It happens that a large proportion of stenoses are formed as eccentric lesions (i.e. lesions that do not extend completely around the circumference of the affected body vessel). A suitable remedy would effectively treat an eccentric stenosis without adversely affecting healthy, non-diseased tissue.

Dilation of stenoses using standard angioplasty balloons has enjoyed widespread acceptance in the treatment of stenoses, however, this treatment protocol suffers from a high rate of restenosis. Recent studies, however, indicate that the rate of restenosis can be reduced if the stenosis that is being dilated is also incised. With incision, some stenoses can be more easily flattened, and the likelihood of damaging the artery during dilation may be reduced.

For the reasons cited above, cutting balloons may be used as a replacement for conventional percutaneous transluminal coronary angioplasty (PTCA) procedures in the revascularization of coronary and peripheral vessels. In particular, the cutting balloon mechanism is unique in that the balloon pressure is distributed over one or more incising elements (e.g. atherotomes). Functionally, the incising elements act as stress concentrators and cut initiators in PTCA atherectomy procedures. In some cases, PTCA atherectomy procedures may be effective in reducing vessel recoil and vessel injury and in lowering the rate of restenosis, as compared to conventional PTCA procedures.

U.S. Pat. No. 5,196,024 which issued to Barath on Mar. 23, 1993 for an invention entitled "Balloon Catheter With Cutting Edge," discloses an inflatable angioplasty balloon having a number of elongated atherotomes (e.g. 8 blades) mounted longitudinally on the surface of the balloon and distributed uniformly around the circumference of the balloon. During an inflation of the Barath balloon, the atherotomes move radially to induce a series of longitudinal cuts into the surface of the artery that are somewhat uniformly distributed around the circumference of the artery. When incising an eccentric lesion, however, it is typically desirable to incise only the diseased portion of the vessel. For these cases, a device designed to incise uniformly around the circumference of the vessel may be unsuitable.

In light of the above, the present invention is directed to unique devices and methods for incising a biological material in a body conduit. In addition, the present invention is directed to directional cutting balloons and corresponding methods of use which are relatively simple to implement and comparatively cost effective.

SUMMARY OF THE INVENTION

The present invention pertains to directional cutting balloons for incising a biological material within a body conduit by moving at least one incising element disposed in the conduit along a pre-selected, substantially radial path into the biological material. For example, in one application of the invention, the cutting balloon can be used to incise an eccentric lesion in a body conduit. In greater structural detail, a directional cutting balloon can include an inflatable balloon having a distal end and a proximal end. The distal end can be attached to a distal tube formed with a guidewire lumen. For the directional cutting balloon, the proximal end of the inflatable balloon can be attached to a proximal tube that is also formed with a guidewire lumen. In one embodiment, both the distal tube and the proximal tube are substantially centered along a common guidewire axis.

For the invention, the inflatable balloon is not centered on the guidewire axis. Instead, the inflatable balloon is offset from the guidewire axis. For example, in one particular embodiment of the invention, the inflatable balloon is formed with a working section that defines a balloon axis. In this embodiment, the working section can be substantially cylindrical shaped. Furthermore, when the balloon having a cylindrical working section is inflated, the balloon axis is aligned substantially parallel to, and offset from, the guidewire axis. With this cooperation of structure, the balloon inflates eccentrically relative to the guidewire axis. For the cutting balloon, at least one incising element, such as a blade having a cutting edge, is mounted on the outer surface of the balloon and extends from the working section thereof.

In one particular embodiment of the cutting balloon, a single elongated blade is mounted longitudinally on the balloon and extends radially (relative to the balloon axis) from the balloon to its cutting edge. For this embodiment, the single blade can be positioned on the balloon with the blade, guidewire axis and balloon axis all substantially located in a common plane. With this structural combination, the blade can be driven away from the guidewire in a pre-selected direction during a balloon inflation. Stated another way, for this embodiment, the blade is advanced in the direction of eccentricity during a balloon inflation.

In another embodiment of the cutting balloon, a plurality of incising elements (e.g. three elongated cutting blades) is mounted longitudinally on the outer surface of the balloon with the incising elements circumferentially spaced-apart.

In one particular construction of the cutting balloon, radiopaque blade pad(s) can be used to mount the incising element(s) onto the outer surface of the inflatable balloon. Fluoroscopy can then be used during a procedure to orient the blade for travel (during a balloon inflation) in a direction toward the targeted biological material.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
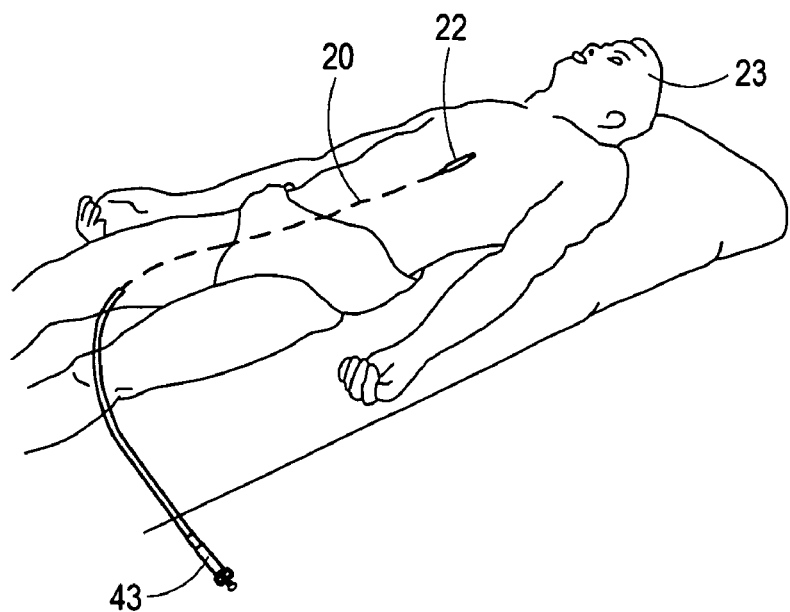
FIG. 1 is a simplified, perspective view of a catheter having a cutting balloon operationally positioned in the upper body of a patient.

Referring initially to FIG. 1, a catheter 20 having a cutting balloon 22 is shown for performing a medical procedure at an internal treatment site of a patient 23. More specifically, the catheter 20 is shown positioned to treat a lesion in an upper body artery of a human patient. Although the catheter 20 is capable of performing a medical procedure in an upper body artery such as a coronary artery, those skilled in the pertinent art will quickly recognize that the use of the catheter 20 as herein described is not limited to use in a specific artery, but, instead can be used in vascular conduits and other ductal systems (e.g. a bile duct or urinary track) throughout the human body. Moreover, although FIG. 1 shows the catheter 20 used in a human body, it is to be appreciated that the catheter 20 can also be used in non-humans (e.g. animals) if desired. Functionally, the catheter 20 is configured to incise a biological material from within a body conduit. As used herein, the term "biological material" and its derivatives includes, but is not limited to, cellular matter including tissue (diseased, healthy or otherwise), deposits such as cholesterol and calcium deposits, and lesions which, for example, may consist of cellular matter and/or deposits.

Figure 2:
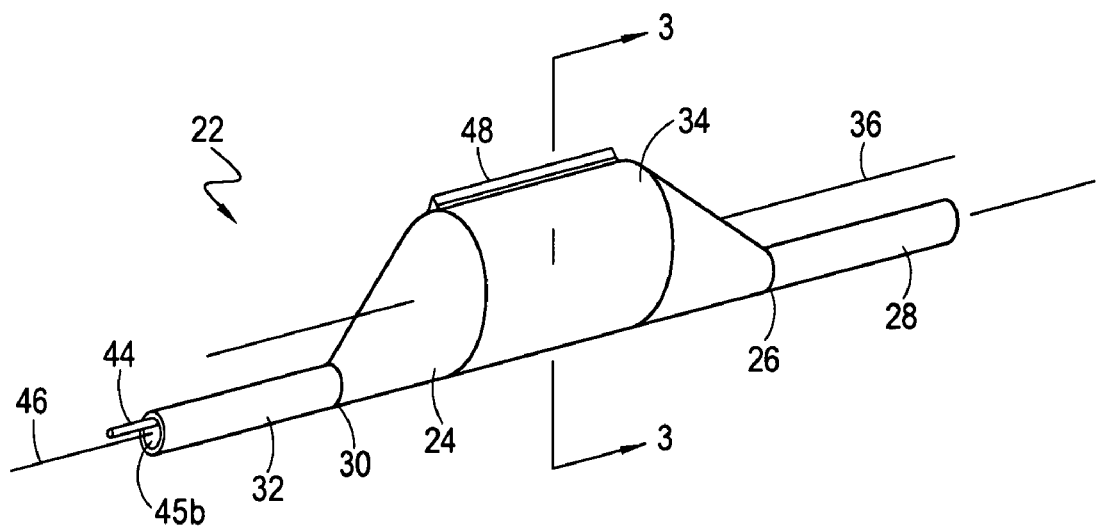
FIG. 2 is an enlarged, perspective view of a cutting balloon.

Referring now to FIG. 2, a distal portion of the catheter 20 is shown to include a cutting balloon 22 having an inflatable balloon 24. The inflatable balloon 24 has a distal end 26 that is attached to a distal tube 28 and a proximal end 30 that is attached to a proximal tube 32. For the embodiment shown in FIG. 2, the inflatable balloon 24 includes a substantially cylindrical shaped working section 34 that defines a balloon axis 36.

For the catheter 20, the inflatable balloon 24 can be made of a compliant, semi-compliant or non-compliant material. Specifically, any suitable thermoplastic or thermosetting material may be used in accordance herewith including both elastomeric and non-elastomeric materials. Thermoplastic materials find particular utility herein. Examples of non-elastomeric materials include, but are not limited to, polyolefins including polyethylene and polypropylene, polyesters, polyethers, polyamides, polyurethanes, polyimides, and so forth, as well as copolymers and terpolymers thereof. As used herein, the term "copolymer" shall hereinafter be used to refer to any polymer formed from two or more monomers.

Examples of suitable elastomeric materials include, but are not limited to, elastomeric block copolymers including the styrenic block copolymers such as styrene-ethylene/butylene-styrene (SEBS) block copolymers disclosed in U.S. Pat. No. 5,112,900 which is incorporated by reference herein in its entirety. Other suitable block copolymer elastomers include, but are not limited to, styrene-isoprene-styrene (SIS), styrene-butadiene-styrene (SBS), styrene-isobutylene-styrene (SIBS) and so forth. Block copolymer elastomers are also described in commonly assigned U.S. Pat. Nos. 6,406,457, 6,171,278, 6,146,356, 5,951,941, 5,830,182 and 5,556,383, each of which is incorporated by reference herein in its entirety.

Elastomeric polyesters and copolyesters may be employed herein. Examples of elastomeric copolyesters include, but are not limited to, poly(ester-block ether) elastomers, poly(ester-block-ester) elastomers and so forth. Poly (ester-block-ether) elastomers are available under the tradename of HYTREL® from DuPont de Nemours & Co. and consist of hard segments of polybutylene terephthalate and soft segments based on long chain polyether glycols. These polymers are also available from DSM Engineering Plastics under the tradename of ARNITEL®.

Non-elastomeric polyesters and copolymers thereof may be employed, such as the polyalkylene naphthalates, including polyethylene terephthalate and polybutylene terephthalate, for example. Polyamides including nylon, and copolymers thereof, such as poly (ether-block-amides) available under the tradename of PEBAX® from Atofina Chemicals in Philadelphia, Pa., are suitable for use herein. Suitable balloon materials are described in commonly assigned U.S. Pat. Nos. 5,549,552, 5,447,497, 5,348,538, 5,550,180, 5,403,340 and 6,328,925, each of which is incorporated by reference herein in its entirety. The above lists are intended for illustrative purposes only, and shall not be construed as a limitation on the scope of the present invention.

Figure 3:
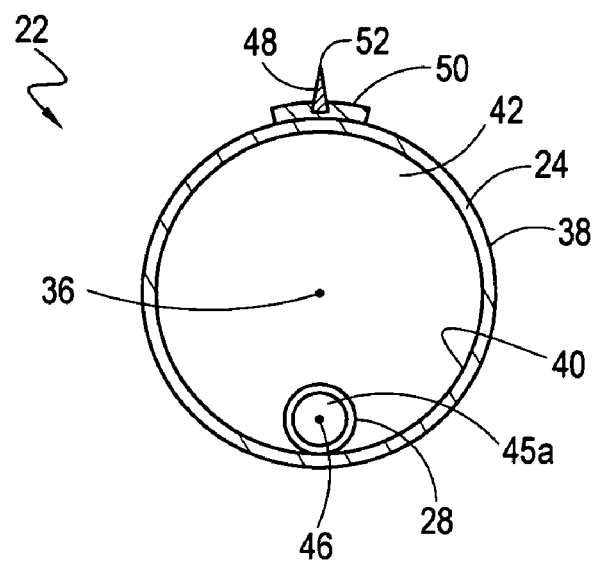
FIG. 3 is a cross-sectional view of the cutting balloon shown in FIG. 2 as seen along line 3—3 in FIG. 2.

As best seen in FIG. 3, the inflatable balloon 24 can be characterized as having an outer surface 38 and an opposed inner surface 40 that surrounds an inflation volume 42. Functionally, the volume 42 can be infused with a medical grade fluid to expand the inflatable balloon 24. More specifically, cross-reference to FIGS. 1 and 2 shows that an inflation device, which for the embodiment shown, is a syringe 43, can be activated to pass a medical grade fluid through an inflation tube 44 (or other suitable lumen) to expand the inflatable balloon 24.

Referring to FIGS. 2 and 3, the distal tube 28 and proximal tube 32 for the embodiment shown are each formed with respective guidewire lumens 45a and 45b. It can be further seen that for this embodiment, the distal tube 28 and the proximal tube 32 are arranged to establish a common guidewire axis 46. The inflatable balloon 24, however, is not centered on the guidewire axis 46. Instead, the inflatable balloon 24 is offset from the guidewire axis 46. Specifically, as shown in FIGS. 2 and 3, the balloon axis 36 is aligned substantially parallel to and offset from the guidewire axis 46. With this cooperation of structure, the inflatable balloon 24 expands eccentrically (i.e. off-center) relative to the guidewire axis 46 during a balloon inflation.

Cross-referencing FIGS. 2 and 3, it can be seen that the cutting balloon 22 further includes an incising element, which in this case is an elongated cutting blade 48. For the catheter 20, the incising element is typically made of a material which is harder than the targeted biological material allowing the incising element to slice or break-apart the biological material. These materials can include, but are not limited to metals, ceramics, polymers such as hardened polymers, composite materials and combinations thereof. For example, the blade 48 can be made of a medical grade stainless steel.

For the embodiment shown in FIGS. 2 and 3, one longitudinally aligned blade 48 is positioned on the eccentric portion of the inflatable balloon 24 and more specifically, is mounted on the working section 34 of the inflatable balloon 24 such that the blade 48, guidewire axis 46 and balloon axis 36 are all located in a common plane. With the interactive cooperation of structure shown in FIGS. 2 and 3, the blade 48 can be driven away from the guidewire axis 46 (and guidewire) in a pre-selected direction during an inflation of the inflatable balloon 24.

In one particular embodiment of the catheter 20, the blade 48 is made of a rigid, radiopaque material allowing the blade 48 to be imaged using fluoroscopy. For example, the blade 48 can be made of a biocompatible metallic alloy composition that is radiopaque in the body in relatively thin sections. One such composition is an iron based alloy that includes approximately 11.0 to 18.0 weight percent Chromium, approximately 8.0 to 12.0 weight percent Nickel, and approximately 10.0 to 35.0 weight percent of one or more high density alloying elements. For the catheter 20, these high density alloying elements can include, but are not necessarily limited to Tungsten, Tantalum, Gold, Palladium, Platinum or Iridium.

As best seen in FIG. 3, a portion of the blade 48 is embedded in a blade pad 50, thereby affixing the blade 48 to the blade pad 50. Functionally, the blade pad 50 can be used to facilitate attachment of the blade 48 to the outer surface 38 of the inflatable balloon 24. Typically, the blade pad 50 is made of a relatively flexible polymeric material, such as one of the balloon materials described above, and is bonded (e.g. heat bonded or adhesively bonded) to the outer surface 38 of the inflatable balloon 24. It can further be seen that the blade 48 extends radially from the blade pad 50 (relative to the balloon axis 36) to an operative surface feature that is capable of incising tissue, which in this case is a cutting edge 52. For the catheter 20, the blade 48 can be formed with a straight, uniform cutting edge 52, as shown, and can be formed with notches, serrations, or any other cutting edge feature known in the pertinent art.

In alternate embodiments of the catheter 20, the incising element can have a shape other than a blade shape. In particular, any incising element that extends to an operative surface feature capable of slicing or breaking apart biological material can be used. For example, the incising element can be formed as a round wire (not shown), or can be an injector (not shown) for injecting a medicament into a pre-selected portion of the vessel wall (e.g. a lesion or healthy tissue). For example, U.S. Pat. No. 6,102,904 which issued to Vigil et al. on Aug. 15, 2000 for an invention entitled "Device for Injecting Fluid into a Wall of a Blood Vessel," and which is assigned to the same assignee as the present invention, discloses an injector system for use with an inflatable balloon. U.S. Pat. No. 6,102,904 is hereby incorporated by reference. As disclosed in Vigil '904, the system includes one or more injectors that extend outwardly from the balloon. A fluid passageway is provided to place each injector in fluid communication with a fluid source. During use of the device, the balloon is first positioned in a vessel proximate the treatment area. Next, the balloon is inflated to embed the injectors into the vessel wall. Subsequently, fluid from the fluid source is introduced into the fluid passageway and through the dispensers into the treatment area.

In one embodiment of the catheter 20, a radiopaque blade pad 50 is used to mount the blade 48 onto the outer surface 38 of the inflatable balloon 24. Fluoroscopy can then be used during a procedure to orient the blade 48 in a direction toward an eccentric lesion. For example, the blade pad 50 can be made of a polymeric material, such as a urethane or other balloon material described above, that is doped with a radio-opaque material. Suitable radiopaque materials include, but are not limited to Tungsten, Tantalum, Gold, Palladium, Platinum or Iridium. Thus, the blade pad 50, the blade 48 or both can be made of radiopaque materials to allow one or more of these structures to be imaged using fluoroscopy. Alternatively, the catheter 20 can include other features known in the pertinent art to include radiopaque markers or bands to position the catheter 20 at a treatment site.

Figure 4:
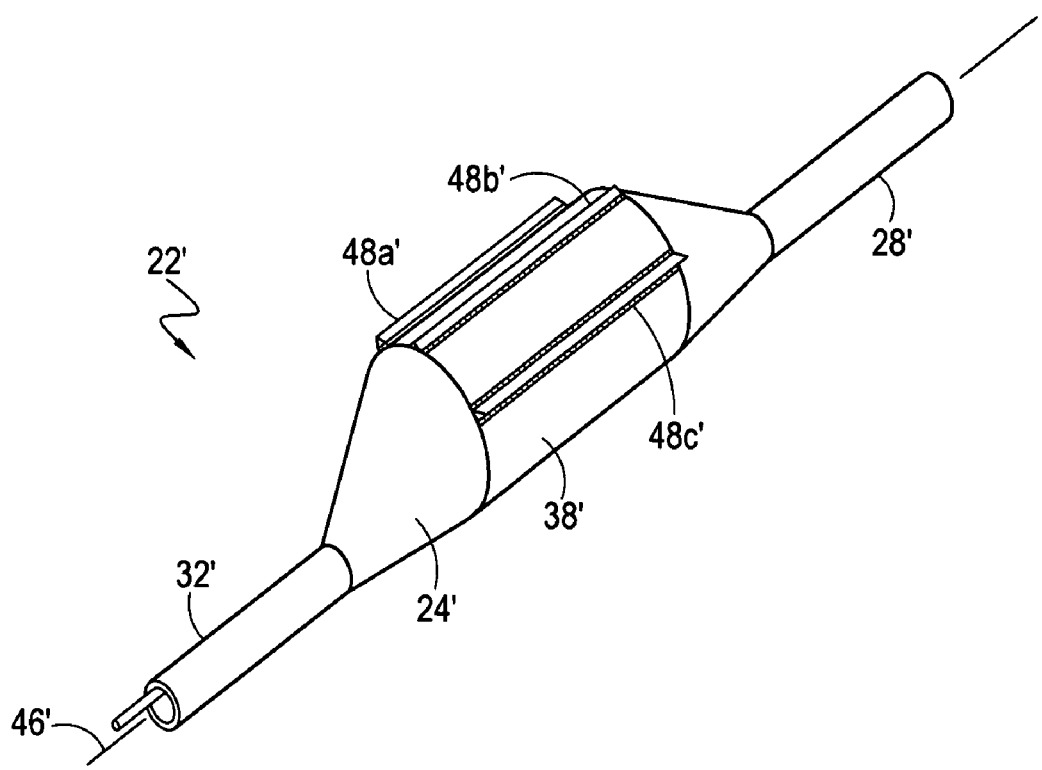
FIG. 4 is an enlarged, perspective view of another embodiment of a cutting balloon having three incising blades.

FIG. 4 depicts another embodiment of a cutting balloon (designated cutting balloon 22') which includes a plurality of incising elements, which in this case is three elongated cutting blades 48a'–48c'. It can be further seen that the elongated blades 48a'–48c' are mounted longitudinally on the outer surface 38' of the inflatable balloon 24' and the blades 48a'–48c' are circumferentially spaced-apart. Also shown, each of the blades 48a'–48c' is mounted on the eccentric side of the inflatable balloon 24' allowing each blade 48a'–48c' to be driven away from the guidewire axis 46' (defined by the distal tube 28' and proximal tube 32') in pre-selected directions during an inflation of the inflatable balloon 24'.

OPERATION

Figure 5A:
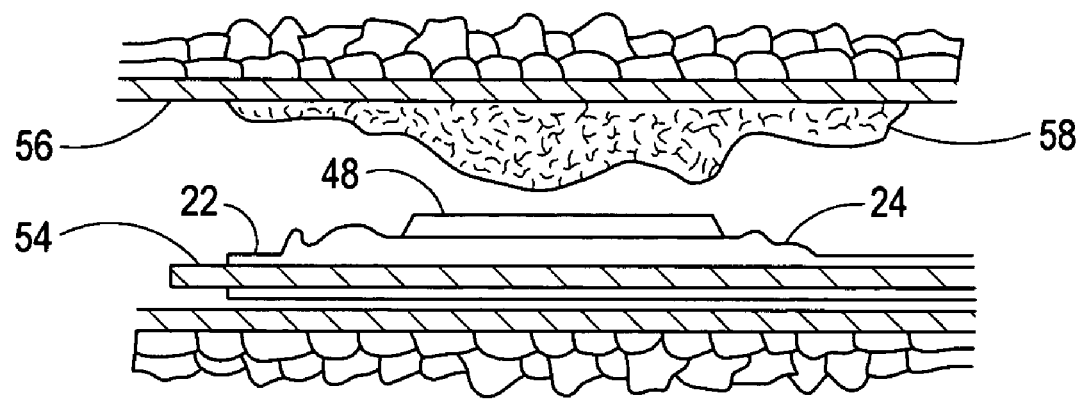
FIG. 5A is an enlarged view of a cutting balloon positioned at a treatment site, shown with the balloon deflated.
Figure 5B:
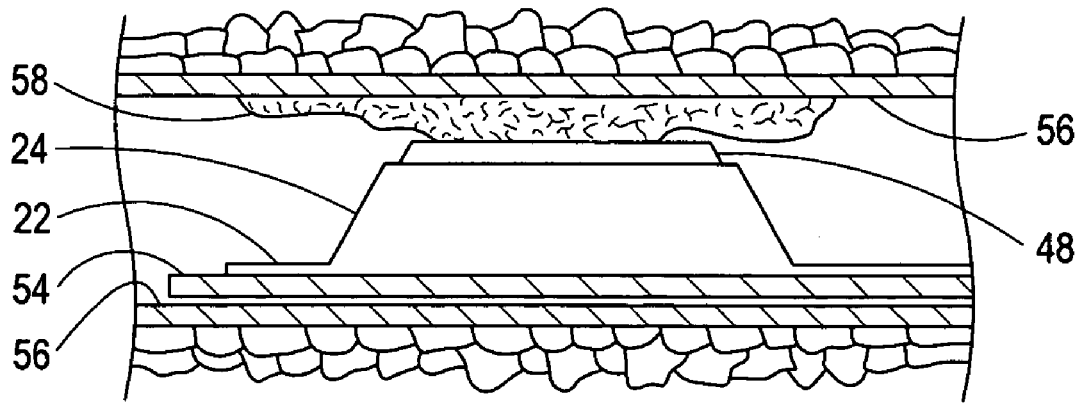
FIG. 5B is an enlarged view of a cutting balloon positioned at a treatment site, shown after a balloon inflation.

A typical use of the catheter 20 can best be appreciated with cross-reference to FIGS. 1, 5A and 5B. In a typical use, the distal end of a guidewire 54 is inserted into the vasculature of the patient 23 using a peripheral artery, such as the femoral artery, for access. The distal end of the guidewire 54 is then advanced past a treatment site, such as the treatment site shown in FIG. 5A, which illustrates a coronary artery 56 that is constricted by a lesion 58. Next, with the cutting balloon 22 deflated, the distal end of the catheter 20 is threaded on the proximal end of the guidewire 54 and advanced along the guidewire 54 until the cutting balloon 22 is positioned across the lesion 58, as shown in FIG. 5A.

Once the cutting balloon 22 is located at the treatment site, fluoroscopy can be used to obtain an image of the guidewire 54 and cutting balloon 22. As indicated above, the blade pad 50 (FIG. 3), the blade 48, or both, can be made of radiopaque materials to allow one or more of these structures to be imaged using fluoroscopy. Using the image, the cutting balloon 22 can be rotated about the guidewire 54 to orient the cutting balloon 22 such that the blade 48 is positioned between the lesion 58 and the guidewire 54. With the cutting balloon 22 properly oriented at the treatment site, the syringe 43 is activated to pass a fluid through an inflation lumen and into the inflatable balloon 24. As the inflatable balloon 24 expands, the blade 48 is directed into and incises the lesion 58, as shown in FIG. 5B.

While the particular Directional Cutting Balloon and corresponding methods of use as herein shown and disclosed in detail are fully capable of providing the advantages herein before stated, it is to be understood that they are merely illustrative of the presently preferred embodiments of the invention and that no limitations are intended to the details of construction or design herein shown other than as described in the appended claims.

What is claimed is:

1. A directional cutting balloon for incising a biological material in a body conduit, said cutting balloon comprising:

a guiding means formed with a lumen for passing a guidewire therethrough, said guidewire defining a guidewire axis;

an inflatable balloon attached to said guiding means, said balloon being formed with a substantially cylindrical shaped working section, with said working section defining a balloon axis, wherein said balloon axis is substantially parallel to and offset from said guidewire axis;

an inflation tube in fluid communication with said inflatable balloon, said inflation tube defining a tube axis, wherein said tube axis is substantially parallel to and offset from said balloon axis; and an incising element mounted on said balloon with said balloon axis located between said guidewire axis and said incising element, and with said incising element extending from said working section to incise the biological material during an inflation of said balloon.

2. A cutting balloon as recited In claim 1 wherein said incising element is a blade having a cutting edge and said blade extends radially relative to said balloon axis from said balloon to said cutting edge.

3. A cutting balloon as recited in claim 2 wherein said blade, said guidewire axis and said balloon axis are all substantially located in a common plane.

4. A cutting balloon recited in claim 2 further comprising a radiopaque blade pad for mounting said blade on said balloon.

5. A cutting balloon recited in claim 4 wherein said blade is made of a polymeric material doped with a radiopaque metal.

6. A cutting balloon recited in claim 1 wherein said cutting balloon comprises a plurality of incising elements, said incising elements being circumferentially spaced-apart on said balloon.

7. A cutting balloon recited in claim 1 wherein said guiding means comprises a distal tube ached to said balloon and a proximal tube attached to said balloon.

8. A cutting balloon as recited in claim 1 wherein said incising element is elongated and mounted on said balloon longitudinally.

9. A cutting balloon as recited in claim 1 wherein said inflatable balloon has a distal end and a proximal end, wherein said guiding means includes a distal tube attached to said distal end of said balloon and formed with said lumen, and wherein said guiding means includes a proximal tube attached to said proximal end of said balloon.

10. A cutting balloon as recited in claim 9 wherein said incising element is a blade having a cutting edge and said blade extends radially relative to said balloon axis from said balloon to said cutting edge.

11. A cutting balloon recited in claim 10 wherein said blade, said guidewire axis and said balloon axis are all substantially located in a common plane.

12. A cutting balloon as recited in claim 10 further comprising a radiopaque blade pad for mounting said blade on said balloon.

13. A cutting balloon as recited in claim 12 wherein said blade is made of a urethane material doped with a radiopaque metal selected from the group of radiopaque metals consisting of Tungsten and Tantalum.

14. A cutting balloon as recited in claim 9 wherein said cutting balloon comprises a plurally of incising elements, said incising elements being circumferentially spaced-apart on said balloon.

* * * * *